United States Patent [19]

Jensen

[11] Patent Number: 4,586,927
[45] Date of Patent: May 6, 1986

[54] IRRIGATION SLEEVE AND ATTACHMENT THEREFOR

[75] Inventor: Ole R. Jensen, Rivervale, N.J.

[73] Assignee: E. R. Squibb & Sons, Inc., Princeton, N.J.

[21] Appl. No.: 293,688

[22] Filed: Aug. 17, 1981

[51] Int. Cl.$^4$ ............................................. A61F 5/44
[52] U.S. Cl. .................................. 604/342; 604/334; 604/341; 604/343
[58] Field of Search ................ 128/283; 604/332–342, 604/343

[56] References Cited

U.S. PATENT DOCUMENTS

| | | | |
|---|---|---|---|
| 3,292,625 | 12/1966 | Marsan | 128/283 |
| 3,385,298 | 5/1968 | Fenton | 604/332 |
| 3,618,606 | 11/1971 | Brown et al. | 128/283 |
| 3,672,370 | 6/1972 | Marsan | 128/283 |
| 3,910,274 | 10/1975 | Nolan | 128/283 |
| 3,916,897 | 11/1975 | Elmore et al. | 128/283 |
| 4,004,589 | 1/1977 | Neumeier | 128/245 |
| 4,050,461 | 9/1977 | Ruby | 128/283 |

FOREIGN PATENT DOCUMENTS

| | | | |
|---|---|---|---|
| 468148 | 9/1950 | Canada | 128/283 |
| 1571657 | 7/1980 | United Kingdom | |

*Primary Examiner*—Thomas Wallen
*Attorney, Agent, or Firm*—Lerner, David, Littenberg, Krumholz & Mentlik

[57] ABSTRACT

An irrigation sleeve for colostomy patients is adapted such that it can be selectively and removeably attached to any one of a plurality of different snap-on attachments, such as an irrigation attachment or a rinsing or flushing attachment. The sleeve is basically funnel-shaped so that it may more effectively direct the flow of irrigating fluid and waste material therethrough. The sleeve has an opening adapted to receive a stoma of a colostomy patient and an opening adapted to receive one of the attachments. The opening for the attachments can be moved out of alignment with the opening for the stoma in order to inhibit soiling of the attachment by irrigating fluid and waste material discharged from the stoma without requiring the attachment to be removed from the sleeve.

15 Claims, 6 Drawing Figures

IRRIGATION SLEEVE AND ATTACHMENT THEREFOR

FIELD OF THE INVENTION

The present invention relates to irrigation devices, and, more particularly, to such devices which are especially adapted for use by colostomy patients to facilitate regular irrigation of the bowel through a stoma.

BACKGROUND OF THE INVENTION

Tumors commonly develop in the large intestine of an individual, thereby requiring the surgical removal of a section of the bowel and the rectum and the surgical formation of an artificial rectal opening or stoma. Such a surgical procedure is called a colostomy.

The stoma does not have a sphincter muscle, which permits a person to voluntarily open and close the rectum. Accordingly, a colostomy patient cannot control the opening and closing of the stoma, which is therefore always open and, hence, susceptible to discharge without warning and without the patient's control.

In order to avoid involuntary bowel movement through the stoma, it is customary and desirable for the patient to periodically irrigate the bowel by taking an enema through the stoma. The bowel is normally irrigated on a daily basis, or perhaps every second day, in order to inhibit involuntary discharges.

In general, the irrigation system employed consists of a water reservoir and means for suspending it at about shoulder level to supply gravity flow of the water through a tube leading from the reservoir to the stoma. A plastic sleeve is adapted to be attached to the patient by, for instance, a supporting belt. An opening at or near the upper end of the sleeve encircles the stoma of the patient. A sealing member associated with the opening forms a fluid-tight seal with the abdominal wall of the patient to protect the patient from spilling or soiling during an irrigation operation. The lower end of the sleeve is open for discharge of the irrigating fluid and waste into a toilet or other receptacle. Provision is made at the upper end of the sleeve for ducting the irrigating fluid through the sleeve and into the stoma.

There are two basic types of irrigation sleeves. One is adapted for use in connection with the open method of irrigation and the other is adapted for use in connection with the closed method of irrigation.

Sleeves adapted for use in connection with the open method are provided with open upper and lower ends. They are also provided with an opening in an inner sidewall a short distance below the open upper end. The open upper end permits the patient to insert his hand into the top of the sleeve for manipulation of a catheter tube or cone through the opening in the inner sidewall and into the stoma prior to supplying irrigating fluid to the stoma through the cone or catheter. Some form of closure means, such as a clip or other device, is employed to close the upper end of the sleeve after the cone or catheter tube is withdrawn at the conclusion of the introduction of irrigating fluid to the bowel through the stoma. The sleeve, with its inner sidewall opening in registry with the stoma, is held in place on the patient by an annular body frame or plate secured by a belt about the patient's waist. One such open system is disclosed in U.S. Pat. No. 3,910,274.

For use in connection with the closed method, the lower end of the sleeve is open. The upper end is, however, closed. A closed irrigation system is usually preferred over an open irrigation system, because the closed system inhibits spilling, splashing, and soiling by inadvertent escape of irrigating fluid or waste through the upper end of the sleeve. The closed system also inhibits the escape of offensive odors. Moreover, in an open system, some form of clip or a similar device is required to close the open upper end of the sleeve, and the attachment of these devices to the sleeve presents a practical problem for the patient.

As indicated above, the introduction of the irrigating fluid into the stoma is made by means of a soft flexible catheter tube or a smooth cone. In the closed method, the catheter tube or cone may be passed through an opening in the outer sidewall of the sleeve, this opening being in registry with the opening surrounding the stoma. Some form of seal or flap is provided in the outer sidewall to prevent the irrigating fluid from escaping through the opening therein as it returns to the sleeve at the completion of the irrigation operation. Such arrangements are shown, for example, in U.S. Pat. Nos. 3,292,625; 3,830,235; and 4,050,461.

Until several years ago, only the catheter method of irrigation was available. More recently, the cone method has been supplanting the catheter method because of its many advantages, such as avoidance of bowel injury and more efficient irrigation performance. When, however, it is desired to use a cone rather than a catheter tube, a much larger opening is required in the outer sidewall of the sleeve, thereby complicating the formation of a fluid-tight seal between the sleeve and the cone to prevent leakage. U.S. Pat. No. 3,830,235 discloses a closed irrigation system which utilizes a cone formed integrally with a sleeve in order to avoid leakage around the cone. The irrigation system of U.S. Pat. No. 3,830,235 is disadvantageous because the cone complicates cleaning of the sleeve. In U.S. Pat. No. 4,050,461, there is disclosed a closed irrigation system in which a cone is removeably attached to a closed sleeve. Because a separate clamping device is required for attaching the cone to the sleeve, the irrigation system of U.S. Pat. No. 4,050,461 is expensive to manufacture and time-consuming to employ. The clamping device also makes the system bulky and cumbersome, thereby rendering it uncomfortable. The flexibility of the cone is important to maximize comfort. Because the cone must be sufficiently rigid to be threaded, its flexibility is severely limited.

Many irrigation sleeves for colostomy patients have, in the past, been designed with straight sidewalls. These straight sleeves, which are shown in U.S. Pat. Nos. 3,292,625; 3,672,370; 3,830,235; and 4,050,461, have two basic disadvantages. First, because they have relatively wide lower ends, relatively large clamps or other sealing devices must be employed in order to close off the lower ends after an irrigation operation. Also, the relatively wide lower ends inhibit the ability of these sleeves to direct the discharged irrigating fluid and waste material into an appropriate receptacle.

Tapered irrigation sleeves, such as the one disclosed in U.S. Pat. No. 3,910,274, have been developed to overcome the problems and disadvantages of the straight irrigation sleeves. However, because the taper of these prior art sleeves extends along substantially their entire length, including the lower ends thereof, these problems and disadvantages are not completely overcome. For instance, because irrigation sleeves are commonly cut to a length which is dependent upon the height of the colostomy patient and/or the height of the receptacle into which the discharged irrigating fluid and waste material are supplied, the sleeves can, in certain situations, be cut so short that their lower ends have a width which approaches the width of the straight sleeves. In such situations, the desirous benefits of having an irrigation sleeve with a relatively narrow lower end would be lost or at least impaired. For example, inasmuch as the shortening of these sleeves changes the width of their lower ends, a variety of different sized clamps may be required in order to close off the lower ends.

It has also been common practice to provide irrigation sleeves with a pair of openings, one opening being adapted to receive the stoma and the other opening being adapted to receive a cone or catheter tube. Because the openings are normally located directly across from each other, the cone or catheter tube, after its removal from the stoma at the conclusion of the introduction of the irrigating fluid to the bowel, is in the flow path of the irrigating fluid and waste material being discharged from the stoma. Thus, the cone or catheter tube can become soiled, thereby requiring its cleaning. If, in order to prevent the soiling of the cone or catheter tube, it is detached from the sleeve, there is a real possibility that discharged irrigating fluid and waste material may escape from the sleeve along with offensive odors.

SUMMARY OF THE INVENTION

The present invention relates to a new and improved irrigation system for colostomy patients who have a surgically formed stoma. In accordance with one aspect of the present invention, an irrigation sleeve includes a pair of ends, at least one of which is closed, and a pair of openings located between the ends of the sleeve. One of the openings is sized and shaped so as to receive the stoma of the patient. A first coupling member is associated with the other opening. The first coupling member is designed to selectively and removeably attach one of a plurality of different snap-on attachments to the sleeve in a fluid-tight manner, thereby inhibiting leakage of fluid from the sleeve at the joint between the sleeve and the attachment. Because the first coupling member is formed integrally with the sleeve, application of the attachment to the sleeve is facilitated by reducing the number of parts which must be handled when applying the attachment to the sleeve.

The snap-on attachment, whether it be an irrigating attachment or a rinsing or flushing attachment, includes a second coupling member which cooperates with the first coupling member to form the fluid-tight seal between the attachment and the sleeve. The second coupling member is formed integrally with the attachment, thereby facilitating application of the attachment to the sleeve by further reducing the number of parts which must be handled when applying the attachment to the sleeve.

In one embodiment, the first coupling member includes a ring which extends outwardly from the sleeve and the second coupling member includes an annular lip which extends radially outwardly from the attachment. The lip includes an annular channel which is sized and shaped so as to releasably and frictionally receive the ring of the first coupling member.

The sleeve has a substantially straight upper section, a substantially straight lower section, and a tapered midsection, which converges towards the lower section. The upper section is wider than the lower section, so that the lower section may more readily direct irrigating fluid and waste material discharged from the stoma into an appropriate receptacle. Because it may be relatively narrow, the lower section is also easier to close off after an irrigation operation. The lower section is long enough so that it may be cut to any one of a plurality of different lengths without enlarging its width. The provision of a relatively wide upper section is advantageous because it facilitates maneuvering of an irrigating attachment during its insertion into the stoma.

The opening in the sleeve for the attachment is movable between the first position in which it is aligned with the opening for the stoma and a second position in which it is not aligned with opening for the stoma. Thus, in its second position, the opening and, hence, the attachment are out of the flow path of the irrigating fluid and waste material being discharged from the stoma, thereby inhibiting soiling of the attachment and escape of irrigating fluid and waste material through the opening. In one embodiment, the opening for the attachment is located at a higher elevation than the opening for the stoma.

BRIEF DESCRIPTION OF THE DRAWINGS

For a more complete understanding of the present invention, reference may be had to the following description of three exemplary embodiments taken in conjunction with the accompanying figures of the drawings, in which.

DESCRIPTION OF THE EXEMPLARY EMBODIMENTS

While the present invention is applicable to an open or closed irrigation system for colostomy patients, it is especially suitable for use in connection with a closed system. Thus, the present invention will be described with particular reference to a closed irrigation system.

Figure 1:
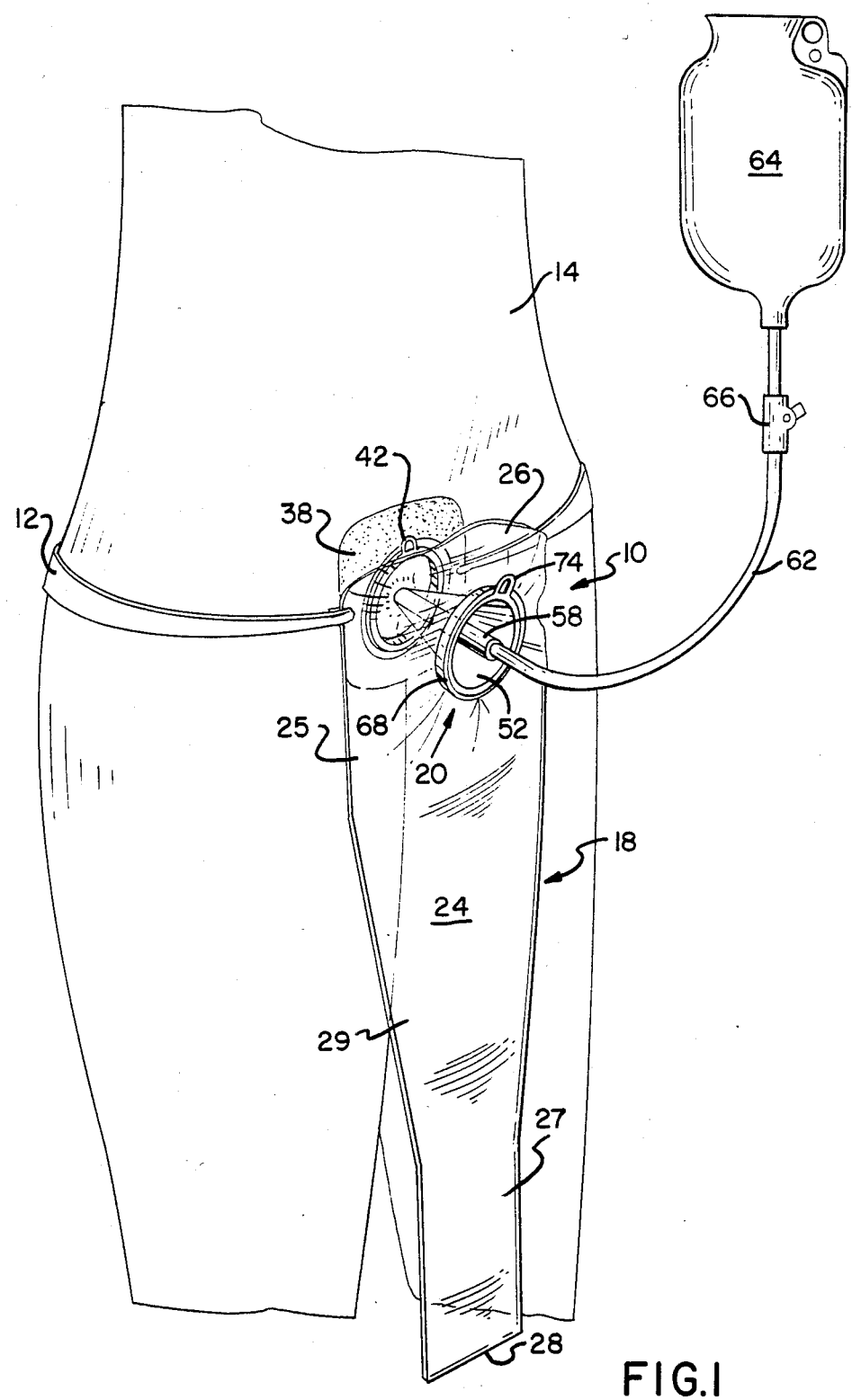
FIG. 1 is a perspective view showing an irrigation device, including a sleeve and an attachment therefor, which is attached to the torso of a colostomy patient who is having irrigating fluid supplied to his bowel through a stoma.
Figures 2, 3, 4:
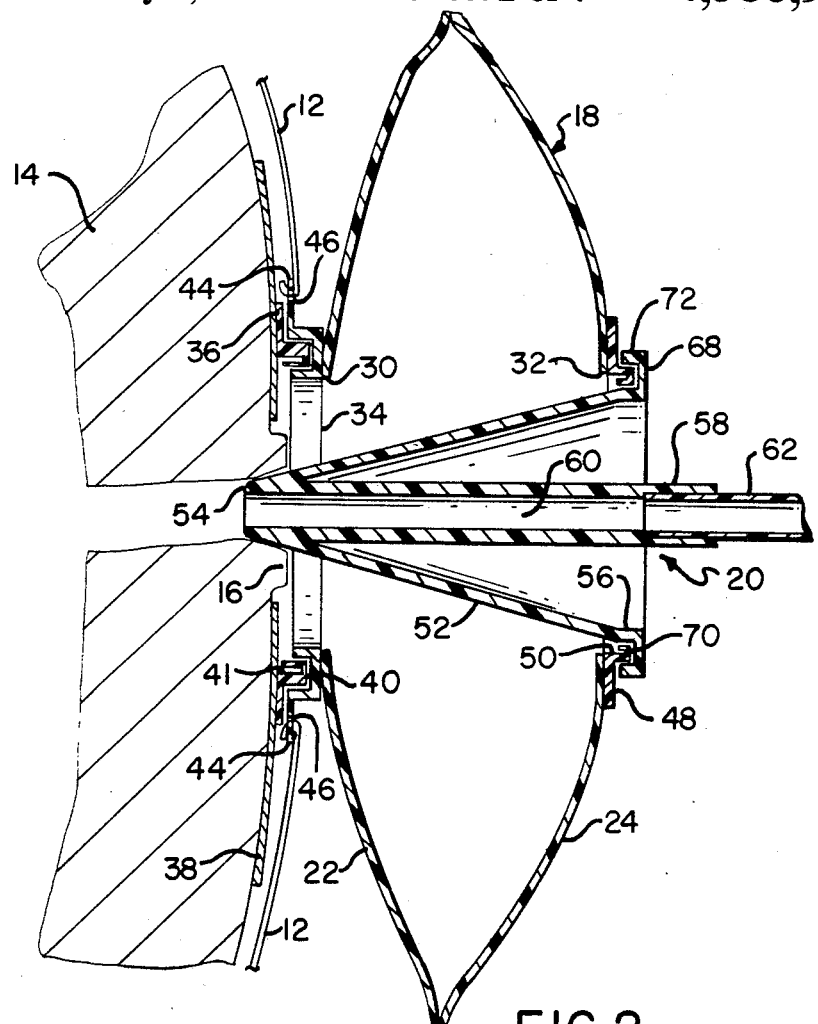
FIG. 2 is a cross-sectional view taken along line I—I in FIG. 1 and looking in the direction of the arrows.
FIG. 3 is a perspective view of a second attachment embodiment constructed in accordance with the present invention, part of the attachment being broken away to facilitate consideration and discussion.
FIG. 4 is a perspective view of a third attachment embodiment constructed in accordance with the present invention, part of the attachment being broken away to facilitate consideration and discussion.

Referring to FIGS. 1 and 2, there is shown an irrigation device 10 attached by a belt 12 to the waist of a colostomy patient 14 who has a stoma 16 (see FIG. 2). The irrigation device 10 includes an irrigation sleeve 18 and a snap-on attachment 20 for the sleeve 18.

Figure 6:
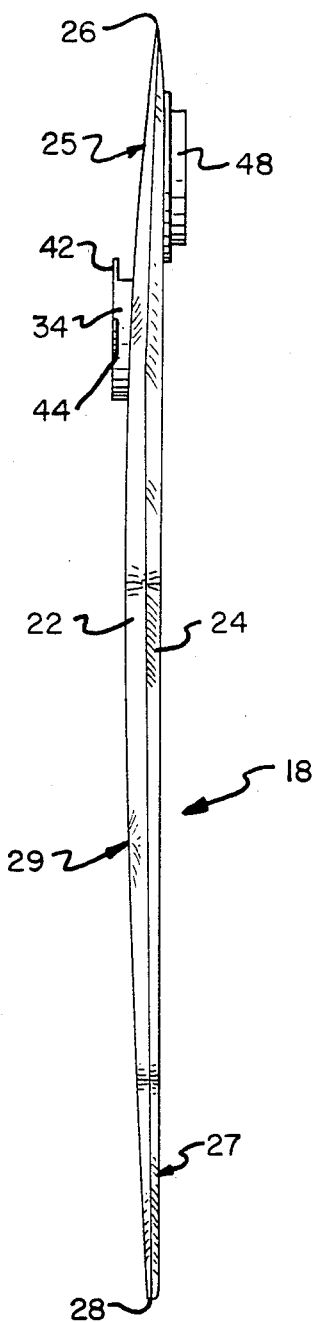
FIG. 6 is a side elevational view of the sleeve shown in FIGS. 1, 2 and 5.

The irrigation sleeve 18, which is preferably made of transparent or translucent plastic, includes an inner sidewall 22 and an outer sidewall 24, which are heat sealed or welded to each other in such a manner that the sleeve 18 has a substantially straight and relatively wide upper section 25, including a closed upper end 26, a substantially straight and relatively narrow lower section 27, including an open lower end 28, and a tapered midsection 29 connecting the upper section 25 to the lower section 27. The upper section 25 is provided with openings 30, 32 formed in the inner and outer sidewalls 22, 24, respectively. The sidewalls 22, 24 are essentially identical except that the opening 32 is located closer to the upper end 26 of the sleeve 18 than the opening 30 (see FIG. 6). The opening 30 is delimited by a plastic coupling member 34, which is heat sealed or welded to the sleeve 18. The coupling member 34 cooperates with a plastic coupling member 36, which is secured to a pad or surgical dressing 38 applied to the abdominal wall of the patient 14 by, for instance, an adhesive (not shown), so that it encircles and seals the area around the stoma 16. An annular channel 40 in the coupling member 34 resiliently receives an annular rib 41 on the coupling member 36. A pull tab 42 and a pair of ears 44 extend radially outwardly from the coupling member 34. Each of the ears 44 has an aperture 46 adapted to receive a corresponding end of the belt 12. The coupling members 34, 36 are more fully described in British Patent No. 1,571,657. Another plastic coupling member 48 delimits the opening 32. The coupling member 48, which is heat sealed or welded to the sleeve 18, includes an annular ring 50 which extends outwardly from the sleeve 18.

The attachment 20 has a cone-shaped body 52 which includes an open small diameter end 54 and an open large diameter 56. A tubular element 58 which is formed integrally with the cone-shaped body 52, extends from the small diameter end 54 past the large diameter end 56. The tubular element 58 has a bore 60 which extends therethrough and communicates with a conduit 62 extending downwardly from a reservoir 64 of irrigating fluid, such as water. The flow of the irrigating fluid from the reservoir 64 to the attachment 20 is controlled by a handoperated valve 66 arranged in the conduit 62. The large diameter end 56 of the coneshaped body 52 includes a radially outwardly extending lip 68 which has an annular channel 70 and an annular skirt 72 extending generally axially towards the small diameter end 54 of the coneshaped body 52. The channel 70 is sized and shaped so as to releasably and frictionally receive the ring 50 of the coupling member 48 when the attachment 20 is snapped onto the sleeve 18, thereby providing a fluid-tight seal between the sleeve 18 and the attachment 20. A pull tab 74 extends radially outwardly from the skirt 72 of the flange 68. The pull tab 74 can be gripped by the patient 14 to assist in the removal of the attachment 20 from the sleeve 18.

Figure 5:
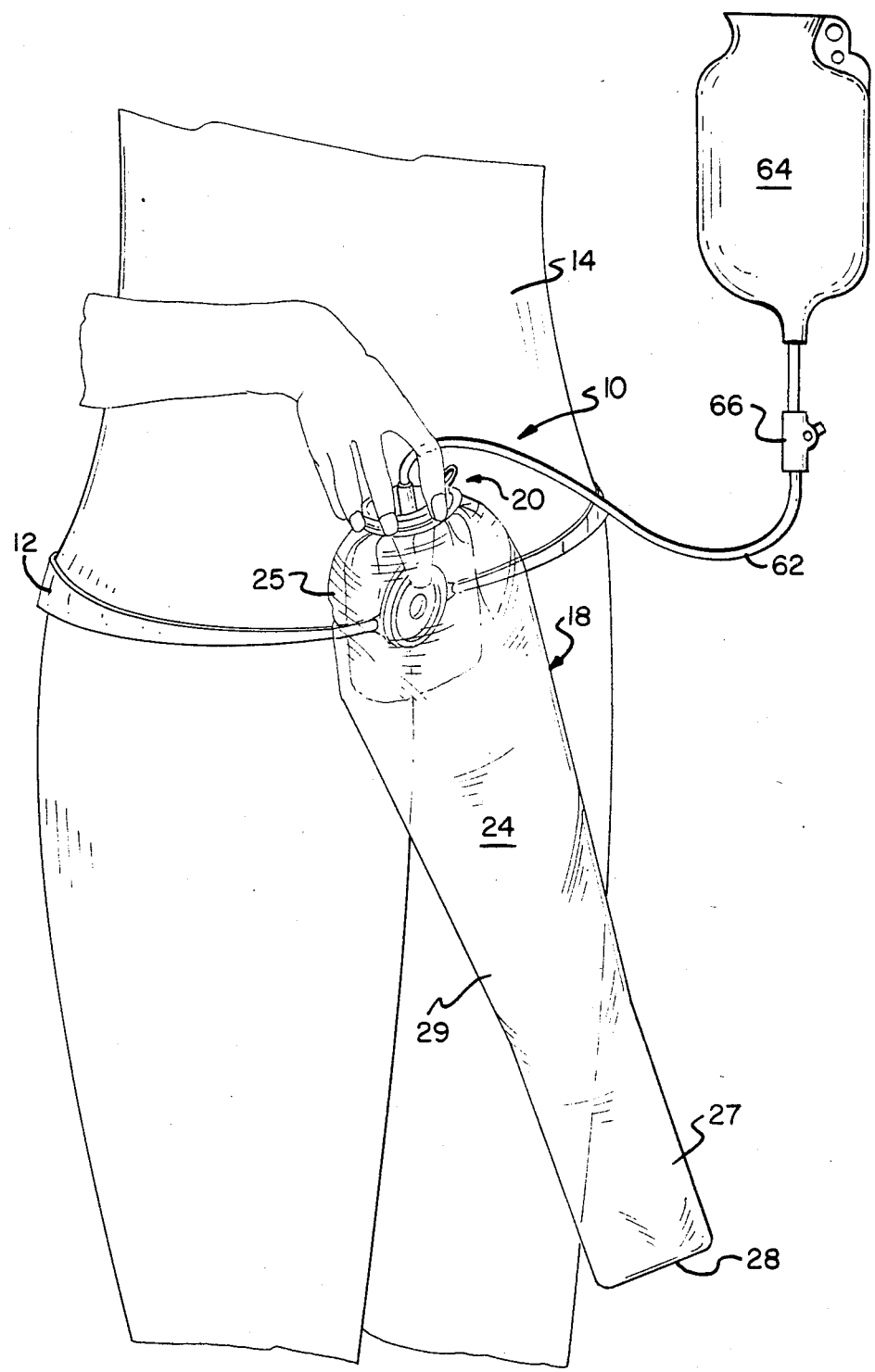
FIG. 5 is a perspective view showing the irrigation device of FIG. 1 in a position it can assume during the discharge of irrigating fluid and waste material from the stoma of a colostomy patient.

In order to perform an irrigation operation, the sleeve 18 is attached to the colostomy patient 14 with the opening 30 surrounding the stoma 16. After the attachment 20 has been coupled to the sleeve 18, the small diameter end 54 of the cone-shaped body 52 is inserted through the opening 30 and into the stoma 16 (see FIG. 1). By opening the valve 66, the patient 14 can actuate the flow of irrigating fluid from the reservoir 64. The irrigating fluid flows through the conduit 62 and the attachment 20 into the stoma 16. As the flow of irrigating fluid continues, it flows into the bowel (not shown) of the patient 14. When a sufficient amount of irrigating fluid has been supplied to the bowel of the patient 14, the flow of irrigating fluid is terminated by closing the valve 66. Upon termination of the flow of irrigating fluid, the attachment 20 is lifted and tilted by the patient 14 in such a manner that it lies against the abdominal wall with its small diameter end pointing generally downwardly (see FIG. 5). This lifting and tiling action not only moves the attachment 20 out of the flow path of the irrigating fluid and waste material being discharged from the stoma 16, thereby preventing its soiling, but also opens the sleeve 18 to facilitate the flow of the discharged irrigating fluid and waste material therethrough. Fluid flow through the sleeve 18 is also facilitated by the funnel shape of the sleeve 18. If the sleeve 18 has to be shortened, it can be, without changing its funnel shape, by cutting off a portion of the lower section 27.

Other exemplary embodiments of different snap-on attachments for the sleeve 18 are illustrated in FIGS. 3 and 4. The various elements illustrated in FIGS. 3 and 4 which correspond to the elements described above with respect to the snap-on attachment 20 of FIGS. 1 and 2 have been designated by corresponding reference numerals increased by 100 and 200, respectively. Unless otherwise stated, the snap-on attachments of FIGS. 3 and 4 operate in the same manner as the snap-on attachment 20 of FIGS. 1 and 2.

Referring to FIG. 3, a snap-on attachment 120 includes a cap-shaped body 152 and a tubular member 158 formed integrally with the cap-shaped body 152. The capshaped body 152 includes an annular lip 168, which is provided with an annular channel 170 and an annular skirt 172. The channel 170 is sized and shaped so as to releaseably and frictionally receive the ring 50 of the coupling member 48 when the attachment 120 is snapped onto the sleeve 18. The skirt 172 is provided with a pull tab 174. By attaching the tubular member 158 to a source of rinsing liquid, such as water, the attachment 120 can be used to clean or flush out the sleeve 18 after an irrigation operation.

In FIG. 4, there is shown a snap-on attachment 220, which includes a solid cap-shaped body 252. The cap-shaped body 252 includes an annular lip 268, which is provided with an annular channel 270 and an annular skirt 272. The channel 270 is sized and shaped so as to releasably and frictionally receive the ring 50 of the coupling member 48 when the attachment 220 is snapped onto the sleeve 18. The skirt 272 has a pull tab 274. The attachment 220 is designed to seal the opening 32 in the sleeve 18 between irrigation operations.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

What I claim is:

1. In combination, an irrigation sleeve for colostomy patients who have a stoma, said sleeve including a pair of ends, at least one of which is closed, a pair of openings located between said ends of said sleeve, one of said openings being sized and shaped to receive the stoma, and a first coupling member formed integrally with said sleeve and surrounding the other opening; and a snap-on attachment for said sleeve, said attachment including a second coupling member formed integrally therewith, said second coupling member cooperating with said first coupling member to form a fluid-tight seal between said sleeve and said attachment when said attachment is snapped onto said sleeve, and supplying means formed integrally with said attachment and fixedly attached thereto for supplying fluid to and through said attachment.

2. A combination according to claim 1, wherein said other opening in said sleeve is sized and shaped so as to receive said attachment.

3. A combination according to claim 2, wherein said attachment includes a flexible, cone-shaped element having an open large diameter end and an open small diameter end sized and shaped so as to be insertable into the stoma through said one opening in said sleeve, and said supplying means includes an open-ended tubular member extending axially within said cone-shaped element from said small diameter end thereof to said large diameter end thereof, whereby said tubular member supplies irrigating fluid to the stoma through said cone-shaped element and said sleeve during a stoma-irrigating operation.

4. A combination according to claim 3, wherein said first coupling member includes a ring which surrounds said other opening and extends outwardly from said sleeve and said second coupling member includes an annular lip which extends radially outwardly from said cone-shaped element, said lip including an annular channel sized and shaped so as to releasably and frictionally receive said ring of said first coupling member.

5. A combination according to claim 4, wherein said lip includes a pull tab, whereby said pull tab may assist in the removal of said cone-shaped element from said sleeve.

6. A combination according to claim 4, wherein said lip is located adjacent to said large diameter end of said cone-shaped element.

7. A combination according to claim 1, wherein said attachment includes a cap having an aperture therein, and said supplying means includes a conduit attached to said cap, said conduit having a bore extending therethrough and communicating with said aperture in said cap, whereby said conduit supplies cleaning fluid to said sleeve through said cap during a sleeve-flushing operation.

8. A combination according to claim 7, wherein said first coupling member includes a ring which surrounds said other opening in said sleeve and extends outwardly from said sleeve and said second coupling member includes an annular lip on said cap, said lip including an annular channel sized and shaped so as to releasably and frictionally receive said ring of said first coupling member.

9. A combination according to claim 8, wherein said lip includes a pull tab, whereby said pull tab may assist in the removal of said cap from said sleeve.

10. A combination according to claim 1, wherein said sleeve has a third coupling member formed integrally therewith, said third coupling member surrounding said one opening and having an annular channel sized and shaped so as to resiliently receive an annular rim of a fourth coupling member attached to a pad or dressing adapted for attachment to a colostomy patient about the stoma.

11. A combination according to claim 1, wherein said other opening and said supplying means are conjointly movable between a first position in which they are aligned with said one opening and a second position in which they are not aligned with said one opening, said second position being remote from said first position, whereby said other opening and said supplying means are out of the flow path of irrigating fluid and waste material discharged from the stoma when said other opening and said supplying means are in said second position.

12. An irrigation sleeve according to claim 11, wherein said one opening is positioned at a first elevation and said other opening is positioned at a second elevation which is different from said first elevation.

13. An irrigation sleeve according to claim 12, wherein said second elevation is higher than said first elevation.

14. An irrigation sleeve according to claim 13, wherein said sleeve has a closed upper end, said other opening being positioned adjacent said upper end of said sleeve.

15. In combination, an irrigation sleeve for colostomy patients who have a stoma, said sleeve including a pair of ends, a pair of openings located between said ends of said sleeve, one of said openings being sized and shaped to receive the stoma, and a first coupling member including a ring formed integrally with and extending outwardly from said sleeve and surrounding the other opening; and a snap-on attachment for said sleeve, said attachment including a flexible, cone-shaped element having an open small diameter end, an open large diameter end, a tubular member extending axially within said cone-shaped element from said small diameter end to said large diameter end, and a second coupling member formed integrally with said cone-shaped element, said second coupling member including an annular lip extending radially outwardly from said cone-shaped element adjacent to said large diameter end thereof, said lip including an annular channel sized and shaped so as to releaseably and frictionally receive said ring of said first coupling member such that said first and second coupling members cooperate with each other to form a fluid-tight seal between said sleeve and said attachment when said attachment is snapped onto said sleeve.

* * * * *